United States Patent [19]
Tabor et al.

[11] 3,954,990
[45] May 4, 1976

[54] BACTERICIDAL AND FUNGICIDAL CYCLIC DIMEDONE DERIVATIVES OF DIALDEHYDES

[76] Inventors: Robert G. Tabor, 1407 W. Tucker Blvd., Arlington, Tex. 76013; Norman Zimmerman, 13 Colby St., Colebrook, N.H. 03576

[22] Filed: Nov. 8, 1973

[21] Appl. No.: 413,806

[52] U.S. Cl. .............................. 424/278; 260/338; 260/340
[51] Int. Cl.² ......................................... A01N 9/28
[58] Field of Search ................................. 424/278

[56] References Cited
OTHER PUBLICATIONS

Chemical Abstracts, 73: 34863f (1970).
Chemical Abstracts 61:7597g (1964).

*Primary Examiner*—Leonard Schenkman
*Attorney, Agent, or Firm*—Amster & Rothstein

[57] ABSTRACT

A novel class of cyclic dimedone derivatives of dialdehydes are useful as antibacterial agents and fungicides. Their high activity and low toxicity make them candidates for replacements for hexachlorophene.

4 Claims, No Drawings

BACTERICIDAL AND FUNGICIDAL CYCLIC DIMEDONE DERIVATIVES OF DIALDEHYDES

This invention relates to a novel class of cyclic dimedone derivatives. More particularly, this invention is concerned with cyclic dimedone derivatives of dialdehydes which are found to possess anti-bacterial and fungicidal activity.

The following compounds are disclosed in U.S. Pat. No. 3,904,693:

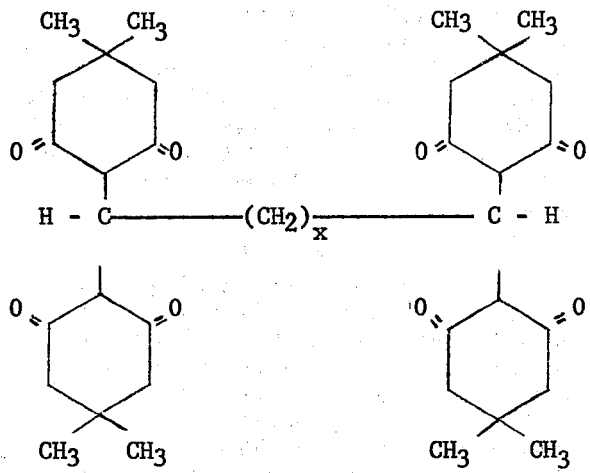

where x is an integer of from 1 to 6. These compounds exhibit strong anti-bacterial activity and negligible toxicity. They are, therefore, potential replacements for hexachlorophene. They are water insoluble. Thus, as does hexachlorophene, they leave an anti-bacterial residue on the skin. However, unlike hexachlorophene, they are not very lipid soluble; thus, they are not readily absorbed through the skin. In addition, these compounds have some fungicidal activity. These compounds are prepared by heating dimedone and a dialdehyde such as glutaraldehyde at reflux for approximately 15 minutes.

It has now been discovered that if the reflux is continued for from two to six hours, preferably at least four hours, a cyclic derivative is formed which has superior anti-bacterial and fungicidal activity.

The cyclic dimedone compounds of this invention have the following structural formula:

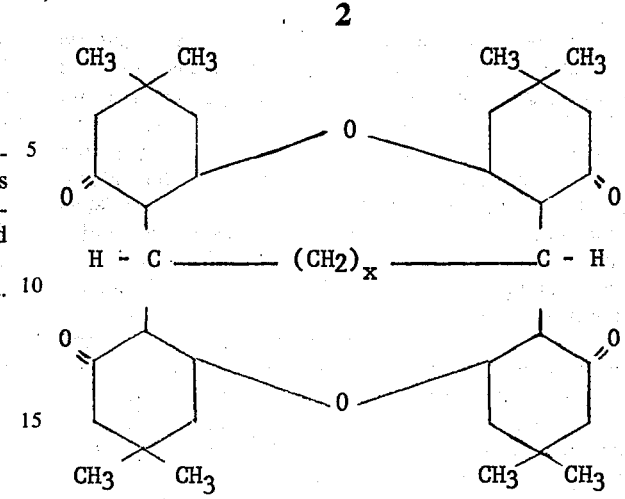

where x is an integer from 1 to 6, preferably from 2 to 4, most preferably 3.

These cyclic compounds can be prepared by reacting a dialdehyde such as glutaraldehyde, succinaldehyde, adipaldehyde, malonaldehyde, or pimelaldehyde with 5,5-dimethyl-1,3-cyclohexanedione (dimedone). The reactants are heated at reflux for at least two hours in a suitable solvent, such as 50% aqueous methanol. The reaction requires four moles of dimedone per mole of the dialdehyde. A slight excess of the dimedone is desirable. Reflux time can be decreased by using small amounts of a hydrochloric acid as a catalyst. The reaction is difficult to control, however, and preferably the cyclic compound is made without a catalyst.

It is preferred that the dialdehyde and dimedone be unsubstituted. However, certain substituents may be added without diminishing the effectiveness of the compound.

An illustrative reaction for preparing the derivatives of this invention is shown by the following equation:

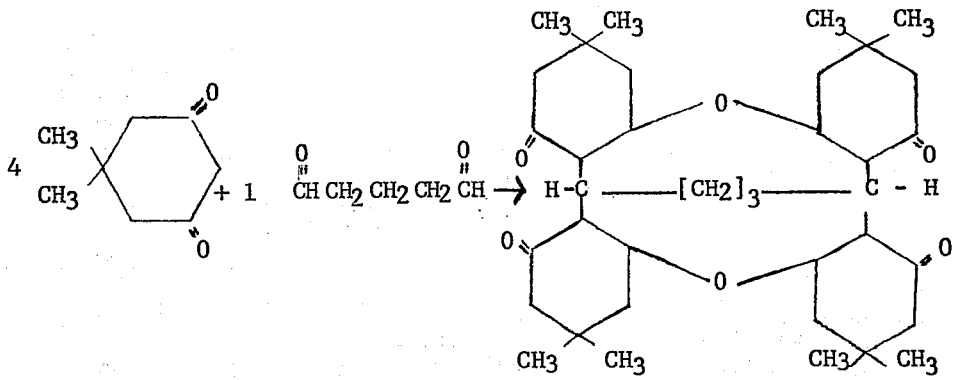

Other cyclic derivatives may be co-produced. They also have fungicidal and anti-bacterial activity. Thus a cyclic compound having a melting point of from 239° to 241°C has been detected which has activity against staphylococcus aureus and streptococcus faecalis.

The cyclic dimedone derivatives of this invention may be applied as a solid (e.g. an aerosol spray) or suspended in a suitable diluent such as water or an isotonic salt solution. The diluted composition should comprise a diluent containing from 0.1 to 10 weight percent of an emulsifier and from 0.1 to 5 weight percent of the cyclic dimedone derivative. The preferred emulsifier is a mixture of polyoxyethylene ethers of mixed partial oleic esters of sorbitol anhydrides available from Sigma Chemical under the trade name "Tween 80" and otherwise known as "Polysorbate 80." This material is commonly used as an emulsifying agent in the preparation of pharmaceuticals. The use in pharmaceutical formulations is discussed in Jowdy, Carolina J. Pharm., 33, 465, 467 (1952). Other suitable diluents include sodium lauryl sulfate and carboxymethylcellulose.

The compounds of this invention have general anti-bacterial activity. They are effective against staphylococcus aureus, pseudomonas aeruginosa, streptococcus faecalis, eschericia coli, etc. The compounds also have fungicidal activity. They are, for example, effective against Mucor Genevensis, Rhizopus Stolonifer, Saccharomyces Cerevisiae, and Candida Albicans.

The invention will be more fully understood by reference to the following Examples which are set forth herein solely for the purpose of illustration.

EXAMPLE I 0.048 moles (i.e., the stoichiometric quantity plus a 20% excess) of dimedone (5,5-dimethyl-1,3-cyclohexanedione) and 0.1 moles of glutaraldehyde are placed into a 50 milliliter flask fitted with a heater and reflux condenser. 30 Milliliters of 50% methanol-water are then added. The mixture is heated at reflux for 4 hours, during which time the reaction product forms and partially precipitates due to its insoluble nature. The reaction mixture is subjected to suction filtration with a Buchner funnel to obtain the product. Yields are quite high because of the insolubility of the product in the reaction solvent. The product is washed in a filter several times with warm 50% methanol-water and air-dried or dried in a vacuum desiccator. The product has a melting point with the range of 209° to 213°C.

EXAMPLE II 0.048 moles (i.e., the stoichiometric quantity plus a 20% excess) of dimedone and 0.01 moles of succinaldehyde are placed in a 50 milliliter flask fitted with a heater and reflux condenser. 30 milliliters of 50% methanol-water are then added. The mixture is heated at reflux for 3 hours. The dimedone derivative of succinaldehyde is insoluble in the solvent and thus partially precipitates from solution even at the reflux temperatures. Suction filtration is applied with a Buchner funnel to obtain the product. Yields are high because of the insolubility of the product in the reaction solvent. The product is then washed in a filter several times with warm 50% methanol-water and air-dried or dried in a vacuum desiccator.

EXAMPLE III 0.048 moles (i.e., the stoichiometric quantity plus a 20% excess) of dimedone and 0.01 moles of malonaldehyde are placed in a 50 milliliter flask fitted with a heater and reflux condenser. 30 milliliters of 50% methanol-water are then added to the solution. The mixture is heated at reflux for approximately 4 hours, during which time the derivative is formed. The derivative is insoluble in the solvent and thus partially precipitates even at reflux temperatures. Suction filtration is performed with a Buchner funnel to obtain the product. As with the glutaraldehyde and succinaldehyde derivatives, yields are quite high because of the insolubility of the product in a reaction solvent. The product is washed in the filter several times with warm 50% methanol-water.

EXAMPLE IV

The cyclic dimedone derivative of glutaraldehyde prepared in accordance with Example I is compared with phenol and hexachlorophene with respect to anti-bacterial activity by the phenol coefficient test. The phenol coefficient test comprises determining the dilution factor of a 5% aqueous phenol solution that is sufficient to kill the bacteria within 10 minutes but not sufficient to kill it within 5 minutes contact time. The same dilution factor is determined with respect to hexachlorophene and the dimedone derivative. The dilution factor of the dimedone or hexachlorophene is then divided by the dilution factor of the phenol to give the phenol coefficient. The cyclic derivative is compared with a derivative prepared by reacting 4 moles of glutaraldehyde with 1 mole of dimedone at reflux conditions for approximately 15 minutes to give the uncyclized derivative. The results are shown in Table I as follows:

Table I

| Organism | Anti-bacterial Activity Phenol Coefficients | | |
|---|---|---|---|
| | Dimedone Derivative | Cyclic Dimedone Derivative | Hexa-chlorophene |
| Staphylococcus Aureus | 16.6 | 13.9 | 13.9 |
| Streptococcus Faecalis | 20.8 | 20.8 | 20.8 |
| Pseudomonas Aeruginosa | <0.66 | 2.0 | 2.0 |
| Eschericia Coli | <0.66 | 2.0 | 2.0 |

EXAMPLE V

The cyclic compound prepared as described in Example I is tested as a fungicide using the phenol coefficient test. Its effectiveness is compared with that of the uncyclized dimedone derivative made by reacting 4 moles of dimedone with 1 mole of glutaraldehyde at reflux for approximately 15 minutes. The results are shown in Table II as follows:

Table II

| Organism | Class | Dimedone Derivative | Cyclic Dimedone Derivative |
|---|---|---|---|
| Mucor Genevensis | Bread Mould | <0.13 | 1.25 |
| Rhizopus Stolonifer | Fungus | <0.13 | 0.83 |
| Saccharomyces Cerevisiae | Yeast | <0.08 | 0.83 |
| Candida Albicans | Yeast Pathogen | <0.10 | 0.66 |

While the invention has been described by means of several specific examples, it is to be understood that modifications and variations of the invention obvious to those skilled in the art may be made without departing from the spirit and scope of the invention.

The embodiments of the invention in which an exclusive property or privilege is claimed are defined as follows:

1. An anti-bacterial and fungicidal composition comprising a diluent, an emulsifier and an effective amount of a compound having the formula:

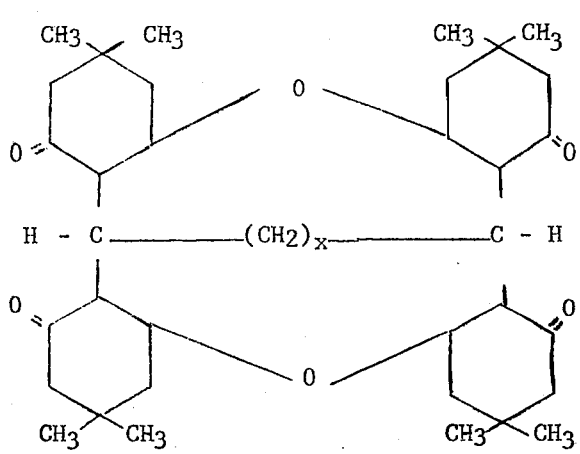

where x is an integer of from 1 to 6.

2. The composition of claim 1 in which said compound comprises 0.1 to 5 wt.% of said composition.

3. A method of killing bacteria comprising contacting the bacterial with an effective amount of a compound having the formula:

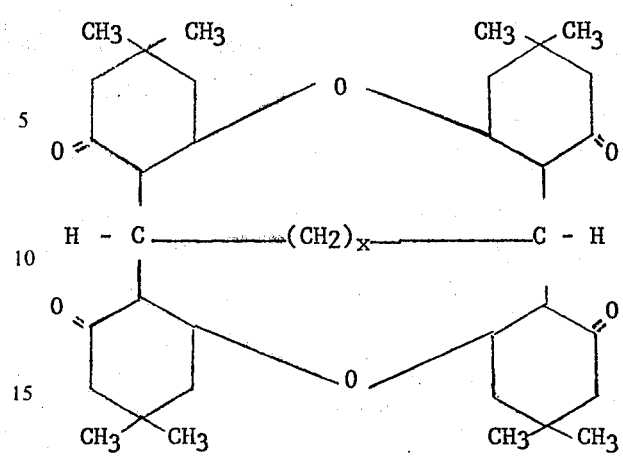

where x is an integer from 1 to 6.

4. A method of killing fungi comprising contacting the fungi with an effective amount of a compound having the formula:

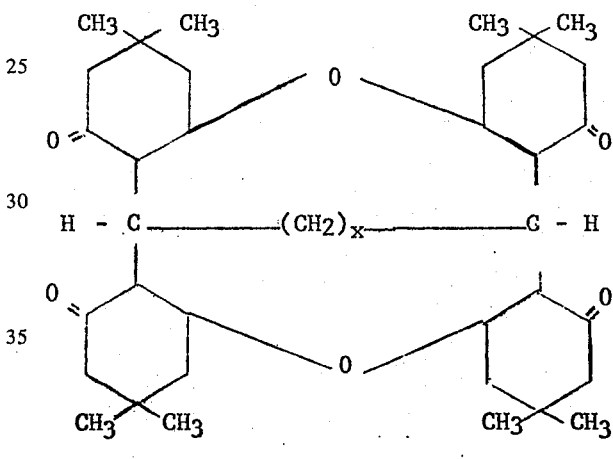

where x is an integer of from 1 to 6.

* * * * *